United States Patent
Pitts et al.

(10) Patent No.: US 9,375,568 B2
(45) Date of Patent: Jun. 28, 2016

(54) CONTROLLING COUGHING AND SWALLOWING

(71) Applicants: University of Florida Research Foundation, Inc., Gainesville, FL (US); The United States of America as Represented by the Department of Veterans Affairs, Washington, DC (US)

(72) Inventors: Teresa Elizabeth Pitts, Gainesville, FL (US); Donald Clementz Bolser, Gainesville, FL (US); Warren E. Dixon, Gainesville, FL (US); Sean Conrad McCoy, Gainesville, FL (US)

(73) Assignees: University of Florida Research Foundation, Inc., Gainesville, FL (US); The United States of America as represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 14/424,551

(22) PCT Filed: Aug. 30, 2013

(86) PCT No.: PCT/US2013/057564
§ 371 (c)(1),
(2) Date: Feb. 27, 2015

(87) PCT Pub. No.: WO2014/036425
PCT Pub. Date: Mar. 6, 2014

(65) Prior Publication Data
US 2015/0209583 A1    Jul. 30, 2015

Related U.S. Application Data

(60) Provisional application No. 61/695,515, filed on Aug. 31, 2012, provisional application No. 61/843,084, filed on Jul. 5, 2013.

(51) Int. Cl.
*A61N 1/36*      (2006.01)
*A61B 5/08*      (2006.01)
(Continued)

(52) U.S. Cl.
CPC .......... *A61N 1/36003* (2013.01); *A61B 5/0823* (2013.01); *A61B 5/4205* (2013.01);
(Continued)

(58) Field of Classification Search
CPC .......... A61N 1/36521; A61N 1/36514; A61N 1/3601; A61N 1/3602; A61N 1/4818; A61N 1/3611; A61N 1/36114; A61N 1/36003
USPC ...................................... 607/20, 42
See application file for complete search history.

(56) References Cited

U.S. PATENT DOCUMENTS 5,397,337 A    3/1995    Jaeger et al.
5,891,185 A    4/1999    Freed et al.
(Continued)

FOREIGN PATENT DOCUMENTS

AU    2013308517    2/2015
AU    2013308517    3/2015
(Continued)

OTHER PUBLICATIONS www.vitalstim.com—VitalStim Therapy—A breakthrough therapy for the treatment of dysphagia, dated Aug. 27, 2012.
(Continued)

*Primary Examiner* — Catherine Voorhees
*Assistant Examiner* — Roland Dinga
(74) *Attorney, Agent, or Firm* — Fleit Gibbons Gutman Bongini & Bianco PL; Paul D. Bianco; Gary S. Winer

(57) ABSTRACT

To protect an airway of a patient, it is important for the patient to be able to swallow and cough effectively. To promote an effective cough or swallow, electrodes are positioned upon skin of the neck of the patient, the electrodes configured for both capturing electromyographic (EMG) information, and for transmitting a stimulating electrical signal to the body. A microphone is positioned upon or near the neck to capture audio information emanating from the body of the patient. Software analyzes the EMG and audio information to identify an attempted or needed cough or swallow, and causes the electrodes to apply an electrical stimulus to the neck of the patient to produce a more efficacious cough or swallow. An additional microphone can be positioned to capture ambient noise, so that such noise can be reduced in the audio information of the first microphone.

20 Claims, 9 Drawing Sheets

(51) Int. Cl.
*A61B 5/00* (2006.01)
*A61N 1/04* (2006.01)
*A61B 5/0488* (2006.01)

(52) U.S. Cl.
CPC ............ *A61B5/4836* (2013.01); *A61N 1/3601* (2013.01); *A61N 1/36014* (2013.01); *A61B 5/0488* (2013.01); *A61N 1/0452* (2013.01)

(56) References Cited

U.S. PATENT DOCUMENTS

| | | | |
|---|---|---|---|
| 7,672,728 | B2 | 3/2010 | Libbus et al. |
| 7,769,461 | B2 | 8/2010 | Whitehurst et al. |
| 7,797,050 | B2 | 9/2010 | Libbus et al. |
| 8,092,433 | B2 | 1/2012 | Hamdy |
| 8,114,030 | B2 | 2/2012 | Ales et al. |
| 8,211,040 | B2 | 7/2012 | Kojima et al. |
| 8,372,020 | B2 | 2/2013 | Martin et al. |
| 9,042,992 | B2 | 5/2015 | Dixon et al. |
| 2002/0133194 | A1* | 9/2002 | Leelamanit ............ A61N 1/36 607/2 |
| 2003/0093128 | A1 | 5/2003 | Freed et al. |
| 2005/0126578 | A1 | 6/2005 | Garrison et al. |
| 2006/0064037 | A1* | 3/2006 | Shalon ................ A61B 5/0006 600/586 |
| 2007/0123950 | A1 | 5/2007 | Ludlow |
| 2007/0150006 | A1 | 6/2007 | Libbus |
| 2008/0234781 | A1 | 9/2008 | Einav et al. |
| 2009/0054980 | A1* | 2/2009 | Ludlow ............ A61H 23/0245 623/9 |
| 2009/0190723 | A1 | 7/2009 | Jang |
| 2010/0125310 | A1 | 5/2010 | Wilson |
| 2011/0009920 | A1 | 1/2011 | Whitehurst |
| 2011/0093032 | A1 | 4/2011 | Boggs, II |
| 2011/0202106 | A1 | 8/2011 | Bolea |
| 2012/0111329 | A1 | 5/2012 | Brand et al. |
| 2012/0253249 | A1 | 10/2012 | Wilson |
| 2013/0079634 | A1 | 3/2013 | Kerber |
| 2014/0016759 | A1 | 1/2014 | Ngar et al. |
| 2014/0046601 | A1 | 2/2014 | Carlsson |
| 2014/0067008 | A1 | 3/2014 | Dixon et al. |
| 2015/0209583 | A1 | 7/2015 | Pitts et al. |

FOREIGN PATENT DOCUMENTS

| | | | |
|---|---|---|---|
| CN | 203436699 | | 2/2014 |
| CN | 104768588 | | 4/2015 |
| EP | 2108313 | | 10/2009 |
| EP | 13832638.4 | | 8/2015 |
| FR | 2946243 | | 12/2010 |
| JP | 5150511113 | | 2/2014 |
| JP | 2015526258 | | 2/2015 |
| WO | 0195666 | | 12/2001 |
| WO | 2005062829 | | 7/2005 |
| WO | 2008048471 | | 4/2008 |
| WO | 2010057286 | | 5/2010 |
| WO | 2011008749 | | 1/2011 |
| WO | WO2011008749 | * | 3/2011 |
| WO | 2011016864 | | 10/2011 |
| WO | 2012134505 | | 10/2012 |
| WO | 2014036425 | | 3/2014 |

OTHER PUBLICATIONS

Wikipedia encyclopedia—Afferent nerve fiber—pp. 2, retrieved Mar. 12, 2014.
Wikipedia encyclopedia—Efferent nerve fiber—pp. 2, retrieved Mar. 12, 2014.
ISR Search Report for PCT/US13/57564, dated Nov. 16, 2013.
Cabre, M., Serra-Prat, M., Palomera, E., Almirall, J., Pallares, R., & Clave, P. (2010). Prevalence and prognostic implications of dysphagia in elderly patients with pneumonia. Age and ageing, 39(1), 39.
Jones, U., Enright, S., & Busse, M. (2011). Management of respiratory problems in people with neurodegenerative conditions: a narrative review. Physiotherapy.
Pitts, T., Troche, M.S., Camaby-Mann, G., Rosenbek, J.C., Okun, M.S., & Sapienza, CM. (2010). Utilizing voluntary cough to detect penetration and aspiration during oropharyngeal swallowing in Parkinson's disease. Chest.
Smith Hammond, C. A., Goldstein, L. B., Homer, R. D., Ying, J., Gray, L., Gonzalez-Rothi, L., & Bolser, D. C. (2009). Predicting aspiration in patients with ischemic stroke: comparison of clinical signs and aerodynamic measures of voluntary cough. Chest, 135(3), 769-777. doi: chest.08-1122 [pii] 10.1378/chest.08-1122.
Smith Hammond, C. A., Goldstein, L. B., Zajac, D. J., Gray, L., Davenport, P. W., & Bolser, D. C. (2001). Assessment of aspiration risk in stroke patients with quantiication of voluntary cough. Neurology, 56(4), 502-506.
Sue Eisenstadt, E. (2010). Dysphagia and aspiration pneumonia in older adults. Journal of the American academy of Nurse Practitioners, 22(1), 17-22.
Van Den Eeden, S.K., et al., Incidence of Parkinson's disease: variation by age, gender, and race/ethnicity. American Journal of Epidemiology, 2003. 157(11): p. 1015-1022.
Brookmeyer, R., S. Gray, and C. Kawas, Projections of Alzheimer's disease in the United States and the public health impact of delaying disease onset. American Journal of Public Health, 1998. 88(9): p. 1337.
Fernandez, H. and K. Lapane, Predictors of mortality among nursing home residents with a diagnosis of Parkinson's disease. Medical science monitor: international medical journal of experimental and clinical research, 2002. 8(4).
Ertekin, C. and J.B. Palmer, Physiology and electromyography of swallowing and its disorders. Suppl Clin Neurophysiol, 2000. 53: p. 148-54.
Jean, A., Brain stem control of swallowing: neuronal network and cellular mechanisms. Physiological Review, 2001. 81(2): p. 929-69.
Canning, B.J., Anatomy and neurophysiology of the cough reflex. Chest, 2006. 129(1 suppl): p. 33S.
Fontana, G.A. and F. Lavorini, Cough motor mechanisms. Respir Physiol Neurobiol, 2006. 152(3): p. 266-81.
Lavietes, M.H., et al., Airway dynamics, oesophageal pressure and cough. Eur Respir J, 1998. 11(1): p. 156-61.
Oku, Y., I. Tanaka, and K. Ezure, Activity of bulbar respiratory neurons during fictive coughing and swallowing in the decerebrate cat. The Journal of Physiology, 1994. 480(Pt 2): p. 309.
Satoh, I., et al., Upper airway motor outputs during sneezing and coughing in decerebrate cats. Neuroscience research, 1998. 32(2): p. 131-135.
Gestreau, C., et al., Activity of dorsal respiratory group inspiratory neurons during laryngeal-induced fictive coughing and swallowing in decerebrate cats. Experimental brain research, 1996. 108(2): p. 247-256.
Lalmohamed A, et al., Causes of death in patients with multiple sclerosis and matched referent subjects: a population-based cohort study. Eur J Neurol., 2012.
Lechtzin N., Respiratory effects of amyotrophic lateral sclerosis: problems and solutions. Respir Care, 2006. 51(8) 371-81.

* cited by examiner

CONTROLLING COUGHING AND SWALLOWING

FIELD OF THE INVENTION

The invention relates to a system and method for protecting the airway, and in particular, promoting an efficacious cough and swallow.

BACKGROUND OF THE INVENTION

A variety of neuromuscular diseases result in dystussia and/or dysphagia (disordered swallow). Recent research in clinical populations has documented that many of these patients have a disorder of airway protection consisting of both dystussia and dysphagia, including amyotrophic lateral sclerosis (ALS), multiple sclerosis, stroke and Parkinson's disease (PD) (Cabre et al., 2010; Jones, Enright, & Busse, 2011; Sue Eisenstadt, 2010; Lechtzin et al., 2006; Lalmohamed A et al., 2012). Voluntary and reflexive cough have been shown to detect and/or predict dysphagia in stroke and Parkinson's disease (Pitts et al., 2010; Smith Hammond et al., 2009; Smith Hammond et al., 2001), and in Parkinson's disease and Alzheimer's disease the leading cause of death is aspiration pneumonia.

The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 CFR §1.56(a) exists.

SUMMARY OF THE INVENTION

In an embodiment of the disclosure, a method of protecting an airway of a patient, comprises monitoring muscles of the patient to detect an attempted cough or swallow; and applying an electrical stimulus to the neck of the patient, varying at least one of an amplitude or frequency over time, the applied electrical stimulus operative to promote an efficacious cough or swallow.

In an embodiment thereof, the method further comprises monitoring audio information of the patient to detect an attempted cough or swallow; and analyzing information pertaining to monitoring muscles and monitoring audio information by at least one computer processor to identify an attempted cough or swallow.

In another embodiment of the disclosure, a method of protecting an airway of a patient, comprises monitoring muscles of the patient to detect an attempted cough or swallow; monitoring audio information of the patient to detect an attempted cough or swallow; analyzing information pertaining to monitoring muscles and monitoring audio information by at least one computer processor to identify an attempted cough or swallow; and applying an electrical stimulus to the neck of the patient if the analysis indicates an attempted cough or swallow, varying at least one of an amplitude or frequency over time, the applied electrical stimulus operative to promote an efficacious cough or swallow.

In various embodiments of the foregoing, the electrical stimulus includes a voltage within a range of greater than zero volts and less than 20 volts; the frequency is varied, and wherein the frequency is swept between at least about 4 Hz to not more than about 30 Hz; an electrical stimulus is applied before the patient has attempted to swallow, and an electrical stimulus is applied between about 1 millisecond to about 0.5 seconds after the patient has attempted to swallow or has swallowed; and the electrical stimulus is applied after a substantial increase in EMG.

In yet further embodiments of the foregoing, monitoring muscles is performed using EMG; sensed EMG information is analyzed by one or more computer processors, the processors operative to initiate the application of the electrical stimulus; monitoring of muscles of the patient is carried out by an electronic device; the patient may indicate to the electronic device that a swallow or cough is impending; the patient may indicate to the processor that a swallow or cough is impending; at least one processor is operative to initiate the application of the electrical stimulus; and the method further includes monitoring environmental ambient audio information and using the at least one processor to reduce an incidence of the ambient audio information in the monitored audio information pertaining to an attempted cough or swallow.

In another embodiment of the disclosure, an airway protection system for protecting an airway of a patient comprises a muscle monitor device configured to communicate information relating to an attempted cough or swallow of the patient; at least one computer processor executing software stored on non-transitory media, the software configured for analyzing information communicated by the muscle monitor device, to identify an attempted cough or swallow; a signal generator configured to apply an electrical stimulus to the neck of the patient responsive to the computer processor if the software analysis indicates an attempted cough or swallow, the signal generator configured to vary at least one of an amplitude or frequency over time, the applied electrical stimulus operative to promote an efficacious cough or swallow.

In an embodiment thereof, the system further comprises an audio monitor device configured to communicate audio information of the patient relating to an attempted cough or swallow; and the software is further configured for analyzing information communicated by the audio monitor device pertaining to identify an attempted cough or swallow.

In another embodiment of the disclosure, an airway protection system for protecting an airway of a patient comprises a muscle monitor device configured to communicate information relating to an attempted cough or swallow of the patient; an audio monitor device configured to communicate audio information of the patient relating to an attempted cough or swallow; and at least one computer processor executing software stored on non-transitory media, the software configured for analyzing information communicated by the muscle monitor device and information communicated by the audio monitor device, to identify an attempted cough or swallow; and a signal generator configured to apply an electrical stimulus to the neck of the patient responsive to the computer processor if the software analysis indicates an attempted cough or swallow, the signal generator configured to vary at least one of an amplitude or frequency over time, the applied electrical stimulus operative to promote an efficacious cough or swallow.

In various embodiments of the foregoing, the muscle monitor device comprises at least two electrodes positionable upon skin of the patient, the at least two electrodes configured for capturing electromyographic information and for transmitting a signal from the signal generator to the body; the audio monitor device comprises a first microphone positioned to capture audio information emanating from the body of the patient; and the software is further configured to analyze the electromyographic with the audio information to identify an attempted cough or swallow, and wherein the processor is configured to cause the signal from the signal generator to be transmitted to the at least two electrodes to apply an electrical stimulus to the neck of the patient if the analysis indicates an attempted cough or swallow.

In yet further embodiments of the foregoing, the system further includes a second microphone configured to capture ambient audio information from outside the body of the patient and the software is further configured for reducing audio information from outside the body, collected by the second microphone, that is present in audio information captured by the first microphone; the first microphone is connected to at least one of the at least two electrodes; the first and second microphones are configured within a single bidirectional microphone; and the bidirectional microphone is connected to at least one of the at least two electrodes.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language). The term "coupled," as used herein, is defined as "connected," although not necessarily directly, and not necessarily mechanically.

In accordance with the disclosure, the airway is protected to improve a state of health of patients, and in the case of certain diseases such as Multiple Sclerosis (MS), Amyotrophic Lateral Sclerosis (ALS), ischemic or hemorrhagic stroke, Parkinson's (PD) and Alzheimer's (AD), to reduce an incidence of aspiration pneumonia and subsequent death resulting from impaired airway protection. Further, the disclosure provides for observing and controlling both cough and swallow in order to ameliorate airway protective disorders, for example in patients with neurodegenerative diseases. For example, PD and AD together affect approximately 6 million people in the United States, and dysphagia and dystussia are primary factors in the death of PD and AD patients. In addition, stroke will affect nearly 1 million people per year in the United States at a cost of 73.7 billion USD for related medical costs and disability (per www.strokeassociation.org, accessed Jul. 15, 2012). MS and ALS affect nearly 0.5 million people in the U.S., however the average life expectancy following ALS diagnosis is approximately 3 years.

Figure 1:
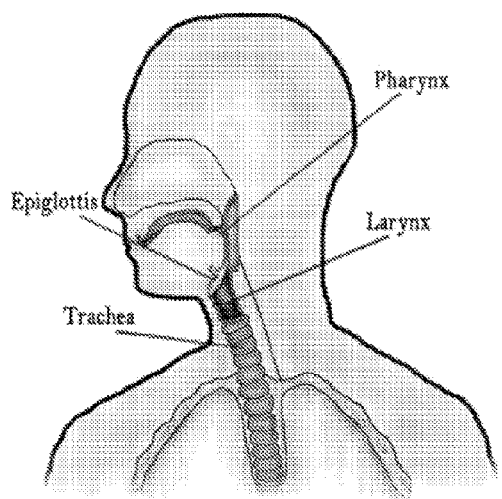
FIG. 1 depicts a prior art diagram of the airway and associated physiological structures of a patient.
Figure 2A:
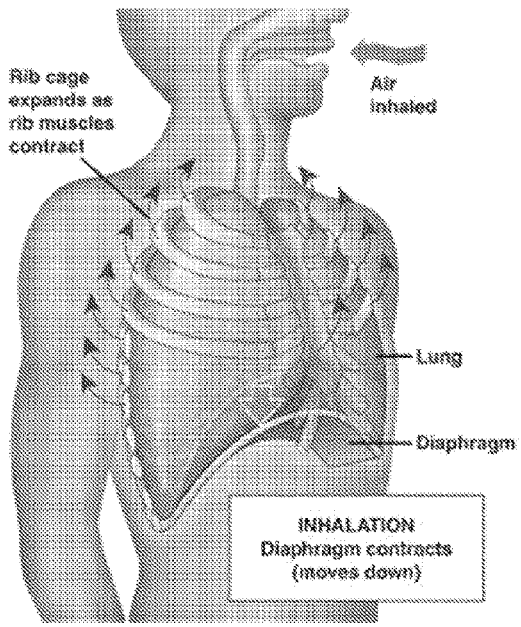
FIG. 2A depicts a prior art diagram of inhalation by the patient.
Figure 2B:
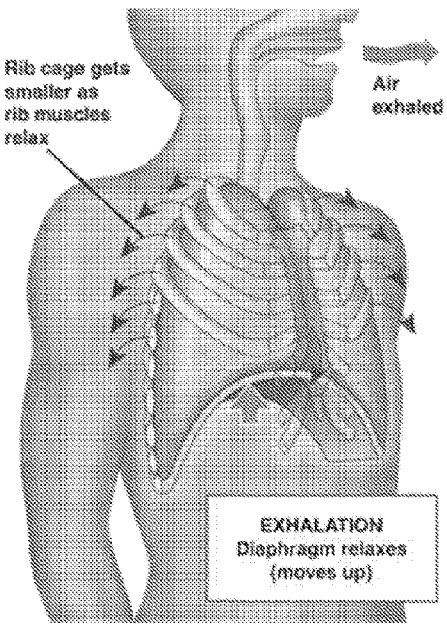
FIG. 2B depicts a prior art diagram of exhalation by the patient.
Figure 3:
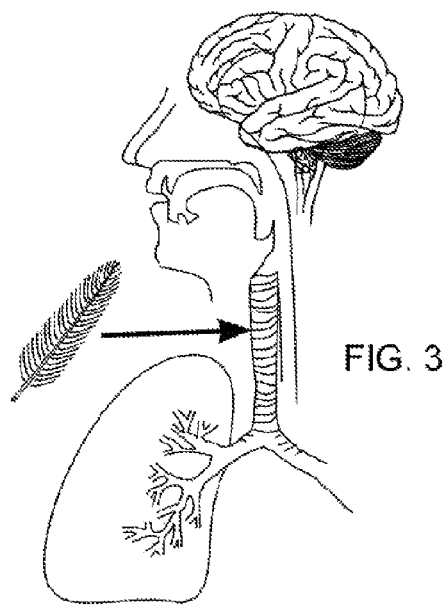
FIG. 3 depicts mechanical stimulation of the trachea to produce a cough or swallow.

With reference to FIGS. 1 and 2A-2B, an overview of certain aspects of the behavior of the respiratory system may be understood, including two phases of breathing. In FIG. 2A, inhalation is illustrated, in which the diaphragm and intercostals muscles contract, and the diaphragm moves down, increasing lung volume. In FIG. 2B, exhalation is illustrated, in which the inspiratory muscles relax, the diaphragm moves up, and lung volume decreases.

Swallowing is a complex coordinated behavior, in which the body normally protects the airway by sealing the trachea to prevent aspiration, or entry of material, into the airway. Dysphagia is a swallowing disorder manifesting an uncoordinated swallowing behavior. Swallowing may be induced by sensory feedback from the tongue, uvula, epiglottis, pharynx, esophagus, or other points of the body. Without being bound to a particular theory, it is considered herein that swallowing mechanisms are coordinated or controlled, at least in part, by a network of neurons within the brainstem, termed behavior control assemblies (BCA's).

Coughing is a defensive reflex triggered, for example, by aspiration. There are typically three phases: (1) inhalation, (2) vocal fold adduction in which the trachea is sealed and pressure is built up in the lungs by contraction of abdominal muscles, and (3) ballistic expiration including a rapid opening of the trachea and an explosive release of air generating high linear airflow velocities and shearing forces that remove material from the airway. Dystussia refers to a coughing disorder, usually resulting in decreased cough strength, or increased compression phase duration (transition time from the inspiratory to expiratory phase). Similarly with respect to swallowing, without being bound to a particular theory, it is considered herein that coughing is also controlled, at least in part, by BCAs. Accordingly, in one embodiment of the disclosure, the brain, and particularly BCAs, are stimulated or influenced by an electrical signal from a system 300 of the disclosure.

Figure 7:
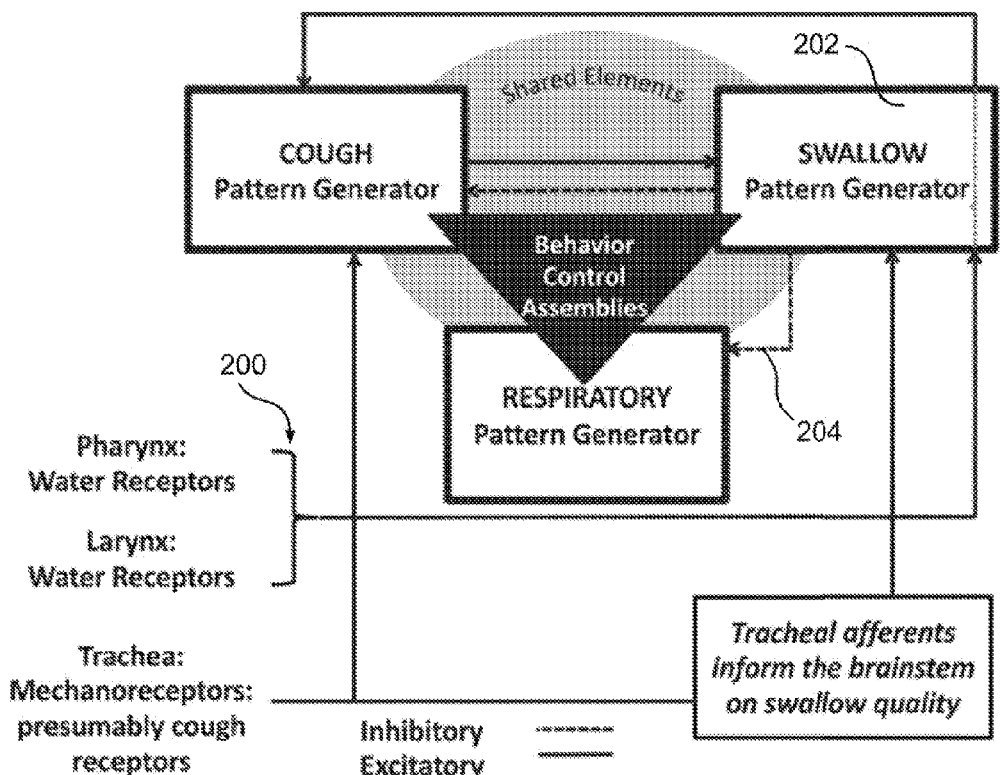
FIG. 7 illustrates inhibitory and excitatory pathways in the patient, and behavior controls, within the patient.

With reference to FIG. 7, an actual or conceptual control pathway is illustrated, the pathway advantageously utilized to carry out the disclosure. In particular, water or liquid receptors in the pharynx and or larynx (200), including areas in the back of the throat or proximate the back of the throat or mouth, trigger swallowing (202), possibly to move material away from the trachea. Accordingly, a disordered swallow, or a simulated disordered swallow, may be used to trigger such response. The triggered swallowing in turn triggers a response in the respiratory system (204) to pause breathing and to seal the trachea (inhibitory), or alternatively to initiate a cough in the event that material has entered the trachea or lungs. In accordance with the disclosure, both excitatory and inhibitory pathways are formed between the swallow pattern generator and the cough pattern generator, wherein a disordered swallow triggers a cough, for example.

In accordance with one embodiment of the disclosure, the patient may initiate a programmed change in the electrical stimulation (for example by pressing a button to produce an efficacious cough and/or swallow. Alternatively, EMG (electromyographic) activity is tracked by a muscle monitoring device of the disclosure, and a programmed change in the electrical stimulation is initiated independent of the patient as described herein. In another embodiment, the patient can indicate to the system that a swallow and or cough is expected, for example prior to eating or drinking, to "presensitize" the system, or alter system parameters to increase a likelihood of electrical stimulation. Such indication may take place in the form of a switch setting on the system, a gesture carried out upon the system, or by the individual, or a spoken command understood by the system. In an embodiment, an audio or acoustic signal is used, possibly in combination with other triggers discussed herein, to indicate that a swallow or cough is expected.

The system and method of the disclosure works to improve airway protection in the manner described herein, regardless of an identification of correct physiological theories. However, it is advantageous to consider, in understanding the disclosure, that it is possible for afferent nerves leading from the throat, trachea, mouth, and or esophagus to communicate information pertaining to the quality of the swallow to the brain, and possibly the BCA area of the brain, which may operate to then trigger coordinated cough and swallow patterns, in coordination with respiratory patterns. In one embodiment, the swallow pattern is coordinated with the cough pattern, to move expelled or invading material into the esophagus, away from the trachea.

Figure 18:
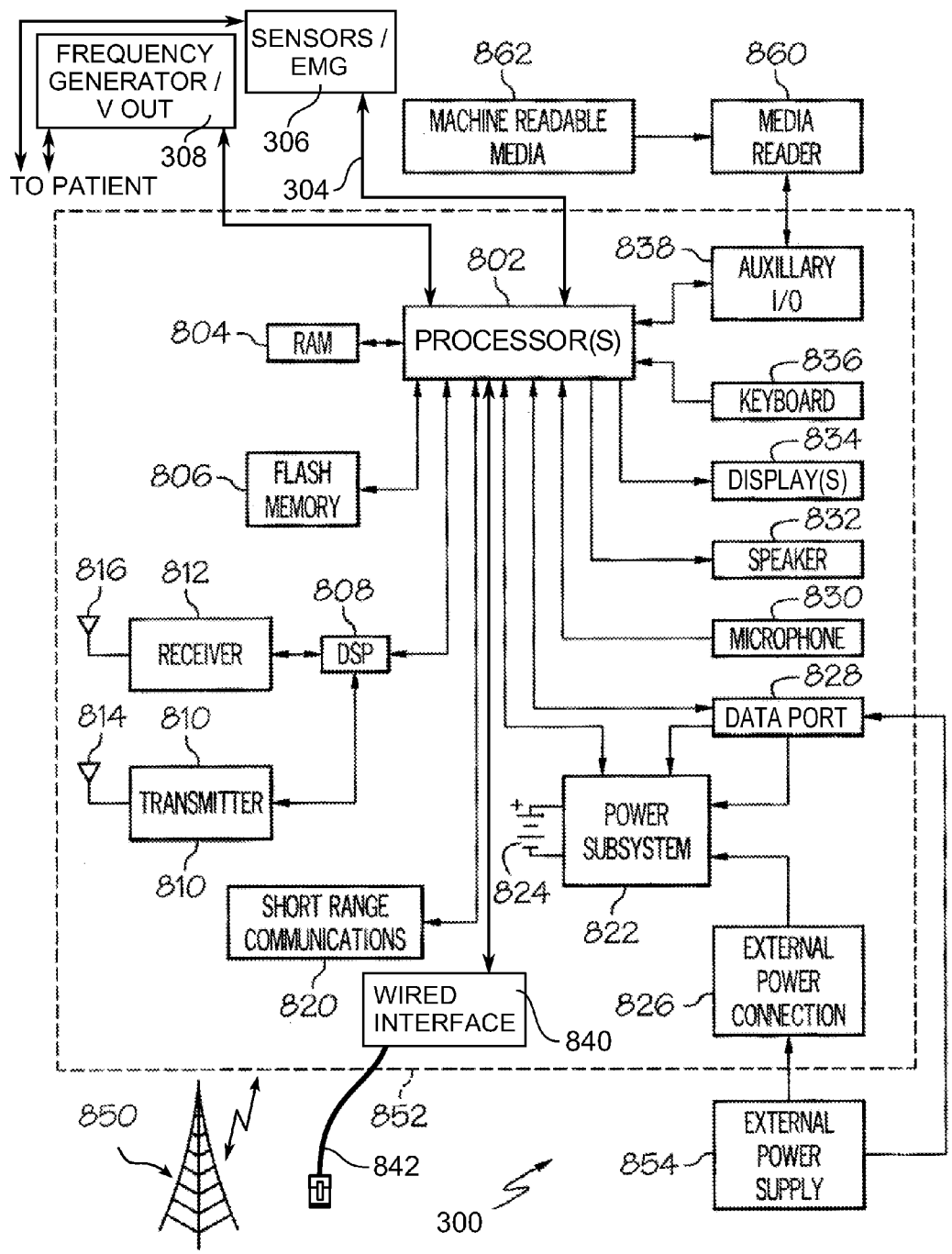
FIG. 18 is a block diagram of components that may be associated with a system of the disclosure.

Thus, in accordance with the disclosure, the trachea is mechanically stimulated (FIG. 18, 310) to stimulate a cough, and in one embodiment, a repetitive cough. Additionally or alternatively, a liquid, such as water, is admitted into the pharynx, for example by injection, triggering a swallow. For testing, injection of fluids may be carried out by a mechanical or robotic fluid introducer device 310 (FIG. 18), including a fluid supply and an applicator, and a hose if the fluid supply is remote from the applicator (not shown). In accordance with the disclosure, an electrical stimulation, advantageously of the superior laryngeal nerve (SLN), promotes either a swallow, cough, or both, advantageously dependent upon stimulation parameters. The electrical stimulation may be provided by a signal generator, for example a frequency generator, and power supply (V out) 308 under control of a processor 802 (FIG. 18). Power for generator/supply 308 may be provided by an onboard battery of a device, or an external power supply. Any or all of these events is advantageously triggered by EMG measurements carried out by sensors and or an EMG device or subunit (FIG. 18, 306), and or esophageal pressure, also measured by sensors 306.

In accordance with the disclosure, a customized or patient specific algorithm will be determined and implemented, based upon successful swallow data. The customized algorithm can be remotely modified by a clinician or other medical practitioner, or may be modified at a clinic, to adapt parameters of the algorithm to the patient's changing medical condition, for example in response to a cold infection, disease progression, further brain injury, or other physiological change.

Figure 4:
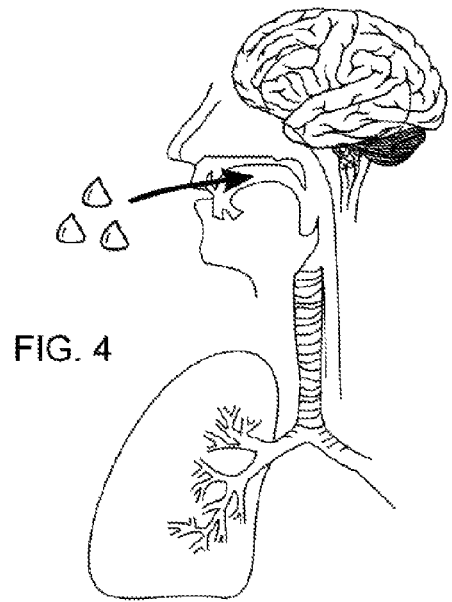
FIG. 4 depicts stimulation of the trachea by introduction of fluids into the mouth of the patient to produce a cough or swallow.
Figure 5:
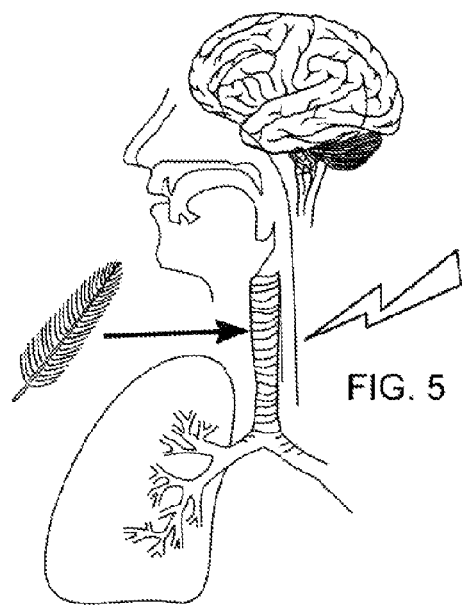
FIG. 5 depicts mechanical stimulation of the trachea to produce a cough or swallow, accompanied by an electrical signal of the disclosure to produce an efficacious cough or swallow.
Figure 6:
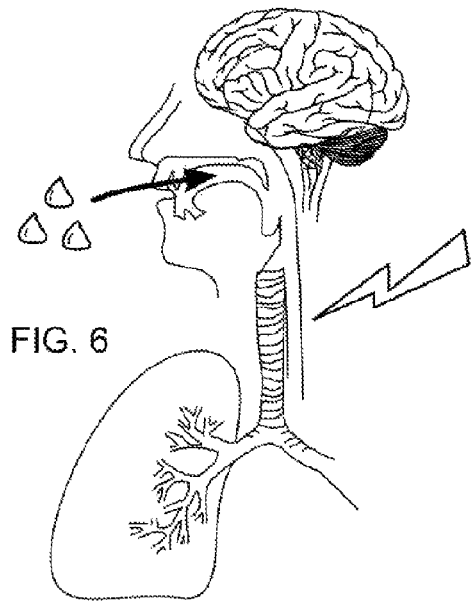
FIG. 6 depicts stimulation of the trachea by introduction of fluids into the mouth of the patient to produce a cough or swallow, accompanied by an electrical signal of the disclosure to produce an efficacious cough or swallow.

Referring now to FIGS. 3-8, it may be seen that the trachea is mechanically stimulated for testing. In the illustration, a feather is illustrated, however it should be understood that mechanical stimulation of the trachea may be carried out by any object, for example by introduction of a thin polymeric cannula. For example, a robotic or mechanical stimulator 312 may be positioned proximate the trachea, inside or outside of the body, under control of processor 802 (FIG. 18). A feather is illustrated because a light and varying mechanical pressure, as in tickling, is advantageous. In FIG. 4, introduction of a liquid to the mouth is carried out, which herein includes the pharynx or back of the mouth. The liquid introduced by any known or hereinafter developed means, including for example a dropper, syringe, or spray nozzle. Introduction of fluid may be carried out, in one embodiment, in response to a detected effort to cough or swallow by the patient. FIGS. 5-6 symbolically indicate the additional use of electrical stimulation, as described herein, in addition to the stimuli described for FIGS. 3 and 4, respectively. The application of an electrical, and EMG measurements, are all advantageously carried out non-invasively, and more particularly, without forming an opening in the patient's body. Similarly, electrical stimulation may be carried out in response to an attempt to cough or swallow by the patient.

In one embodiment, a system of the disclosure is triggered by behavior-specific markers in EMG, to provide behavior-specific programmed surface electrical stimulation routines to shape cough and swallow production. In an embodiment, an audio signal can be captured and analyzed, to thereby be used to trigger electrical stimulation, as discussed further below. An electrical signal is delivered by a plurality of electrodes, and in one embodiment a pair of electrodes, placed in accordance with one embodiment, lateral to the larynx, one electrode placed superior to the thyroid cartilage, and the other electrode placed inferior to the cricoid cartilage. However, it should be understood that other placements may be used. The electrodes may include microphones, as discussed below.

In one embodiment, the voltage and frequency delivered by the electrodes is varied during application. To modify a series of repetitive coughs, for example, a slow waveform is applied, for example a patterned frequency change between 4 to 20 Hz, with an upward ramping of voltage from >0 to 7 volts, is carried out over a period of about 5 to about 20 seconds. In one embodiment, the voltage is as high as 20 volts, and the period as long as 60 seconds. Further, these periods of stimulation may be repeated up to every few minutes for time spans of 24 hours to weeks. It should be understood that the signal generator/power supply 308 may be used to adjust pulse width, frequency, and or amplitude to alter the stimulation for optimal results for a patient. Examples of a patterned frequency change include triangular, sweep, stepped, fixed, various, sinusoid, spike, square, monophasic, and biphasic. In one embodiment, varying the frequency is employed to advantageously decrease a possibility of habituation to the stimulus by the patient. In another embodiment, the signal may be applied for periods longer than 20 seconds, to bring about synaptic plasticity, for example synaptic improvements associated with swallowing, to improve independent functionality of the patient.

It should be understood, however, that patients who present greater barriers to transmission of an electrical signal into the body, for example patients with relatively large amount of adipose tissue, or high skin thickness, may require higher voltages, as determined by the medical practitioner, weighing the patient's individual tolerances and safety.

This stimulus is advantageously triggered by an increase in esophageal pressure, to improve the force and efficacy of a cough. Additionally or alternatively, a patterned frequency change between 4 to 20 Hz is carried out at a constant 5 volts until, for example, about 0.25 to 0.75 seconds after a swallow has occurred. Higher frequencies have also found to be effective, for example about 30 Hz. In accordance with the disclosure, the stimulus develops normal swallows, which are advantageously swallows that move food material at normal speed through the pharynx and are without penetration or aspiration into the vocal folds or trachea. This stimulus is advantageously triggered by an EMG signal indicative of an attempted swallow, and promotes a timely and effective swallow. These frequencies, voltages, and timing are illustrative only, and represent one pattern that has been found to be advantageous for the recited purpose. It should be understood, that significant variations are contemplated. It should further be understood that effective voltages ranges may vary proportionate to the size of the neck, an amount of submental fat, and a thickness of the skin. More particularly, in accordance with the disclosure, it has been found that a novel program of varying frequency and varying voltage (amplitude and or pulse width), generally, can modify the production of a cough, and that a varying frequency and constant voltage, generally, can modify the production of a swallow, and that application of these electrical stimuli are best carried out in response to the body's attempt to initiate a cough or swallow, respectively. These two application modes are embodied within the system to initiate the desired behavior from the patient. Without being bound by a particular theory, it is possible that application of voltage in the manner described above causes a signal to be transmitted along tracheal and esophageal afferent nerves, to the brainstem, thereby modifying the physiological response, and in particular, shaping the production of a cough and or a swallow.

In one embodiment, application of voltage to the patient is in response to an attempt to cough or swallow, as detected by sensors connected to muscles of the patient, advantageously as interpreted by one or more processors. In another embodiment, application of voltage is coordinated with either or both of introduction of fluids to the mouth, or mechanical stimulation of the trachea or other tissue of the neck area, in order to stimulate or promote an efficacious cough or swallow, thereby protecting the airway from the introduction of unwanted material.

Figure 8:
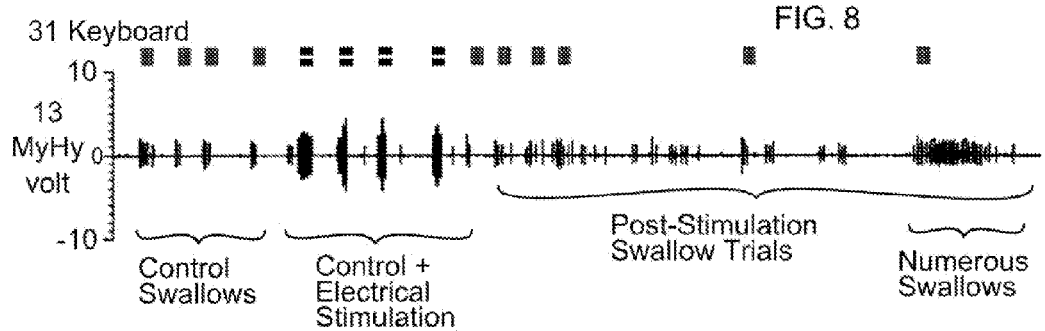
FIG. 8 is a graph of electrical activity of the mylohyoid muscle in with and without electrical stimulation in accordance with the disclosure.

Referring now to FIG. 8, the stimuli of water in the mouth, or a combination of water in the mouth plus electrical stimulation, as described herein, accompanies an attempt to swallow. The graph indicates electrical activity of the mylohyoid muscle (located under the chin) as a marker, or indication of the incidence and force of a swallow. It may be seen that the electrical stimulation as described herein, significantly increases the force of a swallow. It may additionally be seen that surface electrical stimulation increased the excitability of swallow from an injection of water in the mouth during post-stimulation swallowing. In accordance with the disclosure, in patients with impaired swallow, the activity of the muscles generating a swallow is ballistic-like, or spasmotic. However, their duration of activity is very short, on the order of 200 milliseconds, typically.

Figure 9:
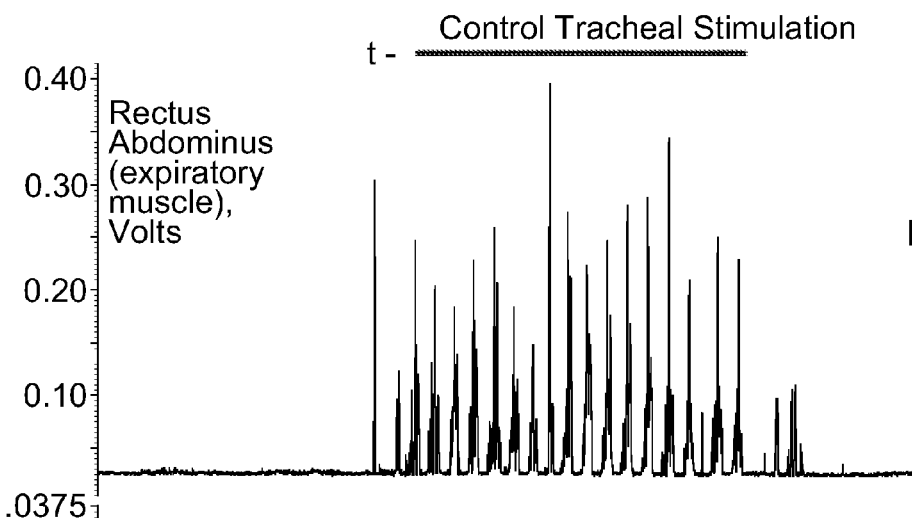
FIG. 9 illustrates a control in which mechanical stimulation is applied to the trachea, and electrical activity of the rectus abdominus muscle is measured.
Figure 10:
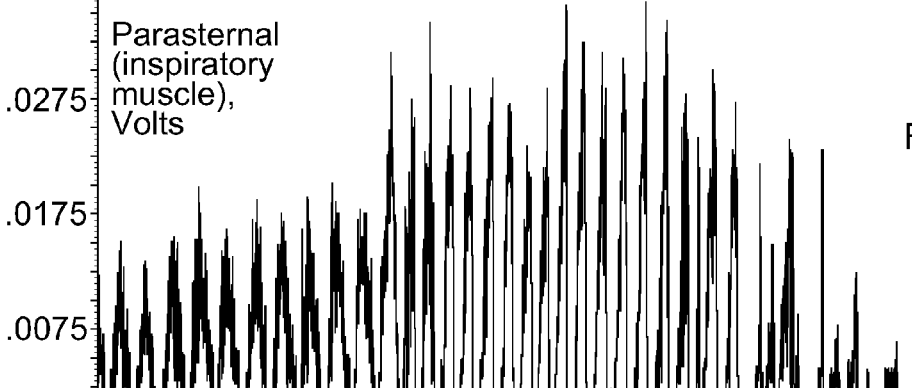
FIG. 10 illustrates a control in which mechanical stimulation is applied to the trachea, and electrical activity of the parasternal muscle is measured.
Figure 11:
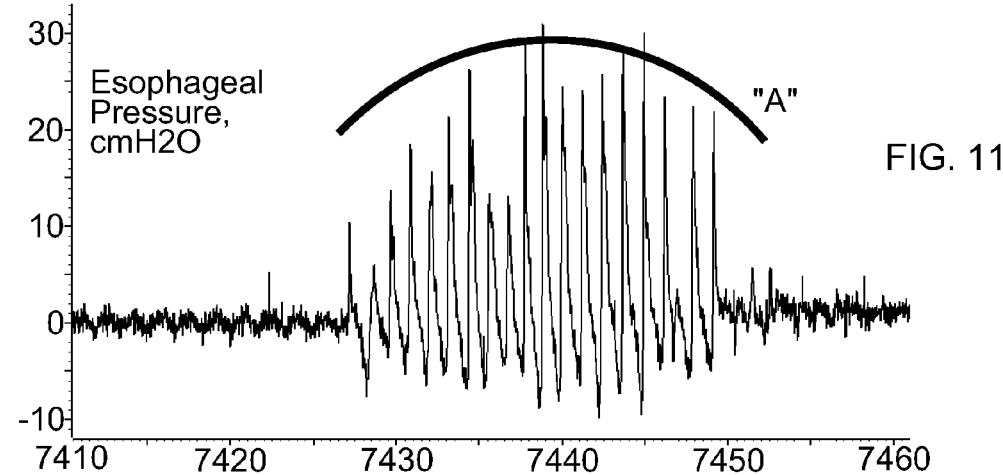
FIG. 11 illustrates a control in which mechanical stimulation is applied to the trachea, and esophageal pressure is measured.
Figures 12, 13, 14:
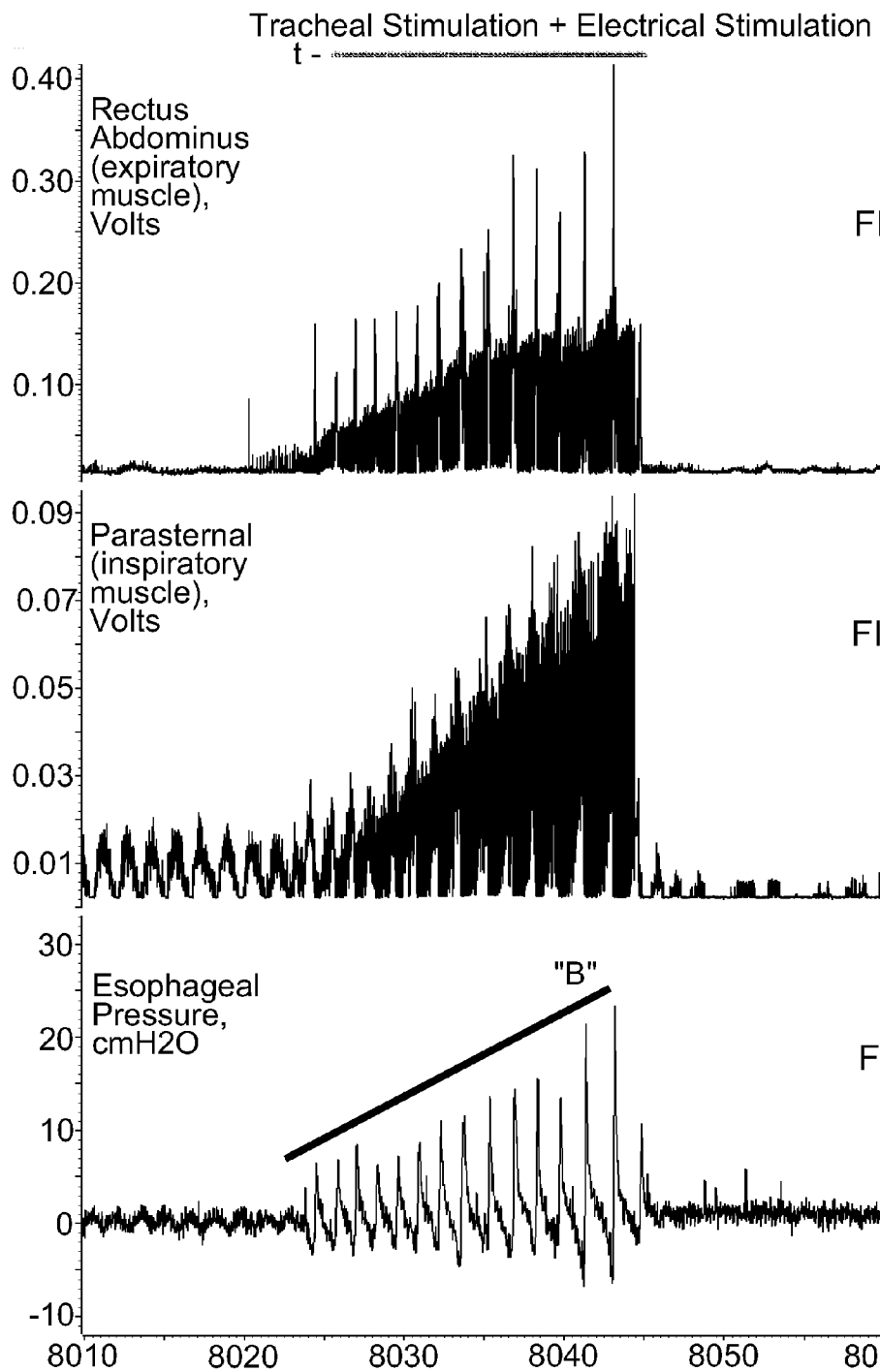
FIG. 12 illustrates a mechanical stimulation applied to the trachea, with electrical stimulation in accordance with the disclosure, wherein electrical activity of the rectus abdominus muscle is measured.
FIG. 13 illustrates a mechanical stimulation applied to the trachea, with electrical stimulation in accordance with the disclosure, wherein electrical activity of the parasternal muscle is measured.
FIG. 14 illustrates a mechanical stimulation applied to the trachea, with electrical stimulation in accordance with the disclosure, wherein esophageal pressure is measured.

In FIGS. 9-14, electrical stimulation to the neck, in which the stimulus was linearly increased over the 20 second period, changed the cough expiratory phase motor drive. In FIGS. 9-11, control mechanical tracheal stimulation is illustrated. It may be seen in FIG. 11 that pressure within the esophagus follows a curved pattern (curve "A"), with pressure gradually increasing, and then gradually decreasing. In FIGS. 12-14, electrical stimulation as described herein is applied, together with tracheal stimulation, producing a ramped increase (line "B") in esophageal pressure, resulting in a more progressive and effective cough.

Monitoring is advantageously carried out by a computer processor coupled to sensors 306 (FIG. 18) configured to detect electrical or other signals generated by the patient. The computer processor analyzes the signals and implements the stimuli in accordance with the disclosure, to improve the timing and efficacy of the cough and swallowing responses, thereby protecting the airway to the therapeutic benefit of the patient.

Figure 15:
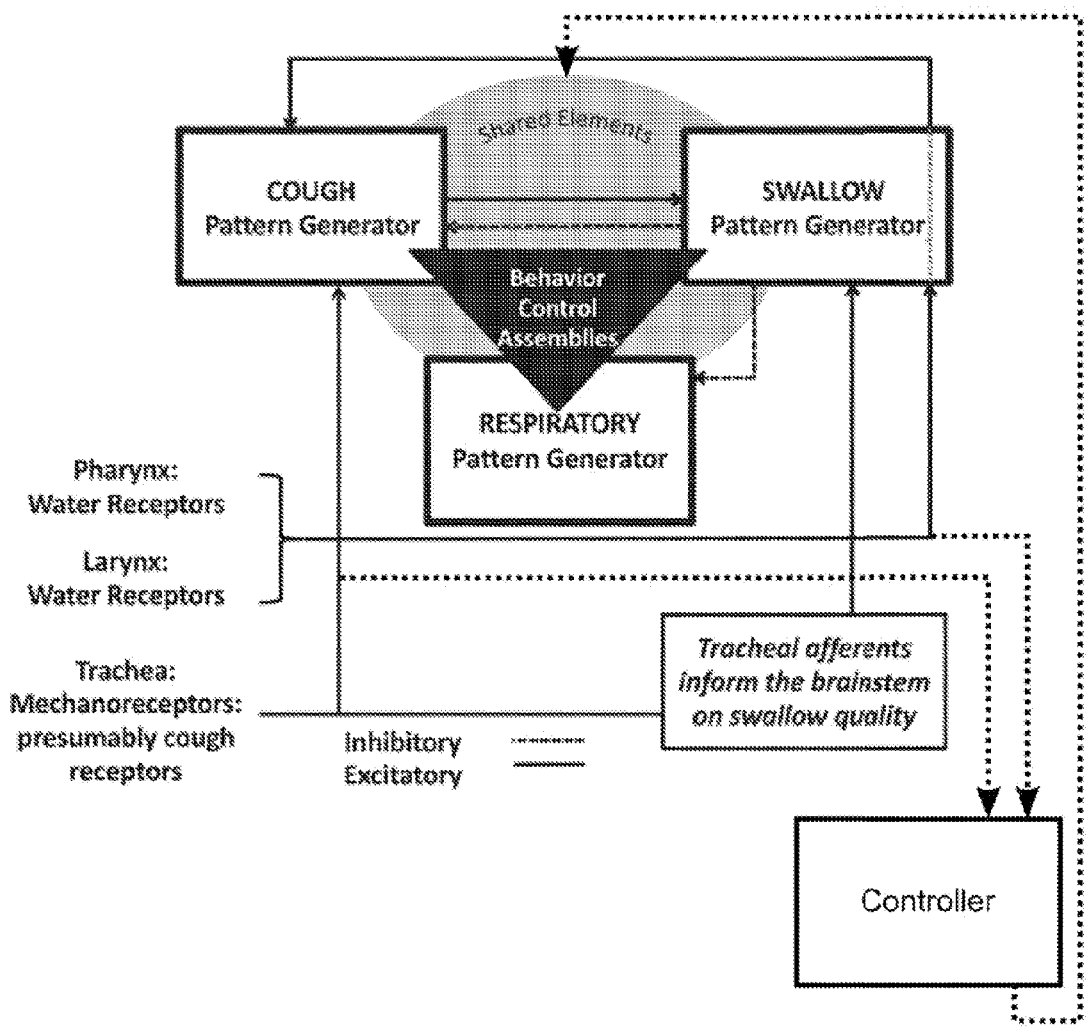
FIG. 15 illustrates inhibitory and excitatory pathways in the patient, and behavior controls, within the patient, including a controller of the disclosure.

In FIG. 15, it may be seen that a model used by the disclosure, as described in the context of FIG. 7, may be combined with a controller, for example a computer having a computer processor 802 (FIGS. 16-18), to form a closed-loop electrical stimulation control strategy to regulate the expression of coughing and swallowing, as described herein. The controller receives inputs from receptors in the pharynx and the larynx, for example as monitored by EMG, and the controller stimulates coughing, swallowing, and respiration using an imposition of electrical signals. The controller then measures the effect of these actions, and adjusts subsequent actions accordingly, to arrive at well timed and effective airway protection, including for example sealing of the trachea, coughing to remove contaminants within the airway, and swallowing to remove the contaminants from the pharynx. The system may further synchronize with respiratory patterns of the patient in real time, through EMG. In an embodiment, the controller and associated processor 802 receives audio signals, including bidirectional audio signals, which can be used to indicate an appropriate time to trigger a cough or swallow, based upon sounds detected, as described further below.

Stimulus parameters of systems of the disclosure shape motor responses to improve impairment of the execution of swallow and cough. Systems of the disclosure may be optimized for either clinical or home based use. For example, clinical devices may be constructed with more rugged or durable materials to withstand greater use, or may enable a wider array of configuration parameters, with respect to home based devices. In either configuration, devices assist a patient with protecting their airway, including assisting a patient with any of swallowing, weaning from mechanical ventilation, and coughing.

In one embodiment systems include wearable micro-chip controlled multi-modal device(s) including a stimulation array that is self-controlled, or may be wired or wirelessly controlled or in communication with other electronic devices. For example, systems of the disclosure may be controlled through a mobile or web based application on a cell phone or other computing device. It is estimated that approximately 15 million people in the United States have symptoms of dysphagia and dystussia (disorder of cough). Accordingly, systems of the disclosure are adjustable for a wide variety of patient physiology, including a broad range of sizing support and electrical power output.

In an embodiment, the system of the disclosure provides a multi-modal stimulation array that is optimized to the patient's physiology based upon real time behavioral feedback from EMG, advantageously surface EMG, but intramuscular EMG may also be used. Advantageously, systems of the disclosure are light weight and or small in size, so that they may be wearable unobtrusive. It is further advantageous if they may be programmed through a wired or wireless connection to a computer or other electronic controller, so that the systems may remotely optimized to changes in a patient's condition. Optimization may thus be accomplished using an onboard controller of the system, or exclusively with a remotely connected controller, or by a combination of the two, to increase airway protection and reduce aspiration-related conditions. Wireless protocols include, for example, WiFi, Bluetooth, 4G, or any other wireless technology known or hereinafter developed.

Systems of the disclosure are advantageously positioned used in combination with other forms of therapeutic treatment, including swallowing and coughing exercises either during or in between uses of the system.

Figure 16:
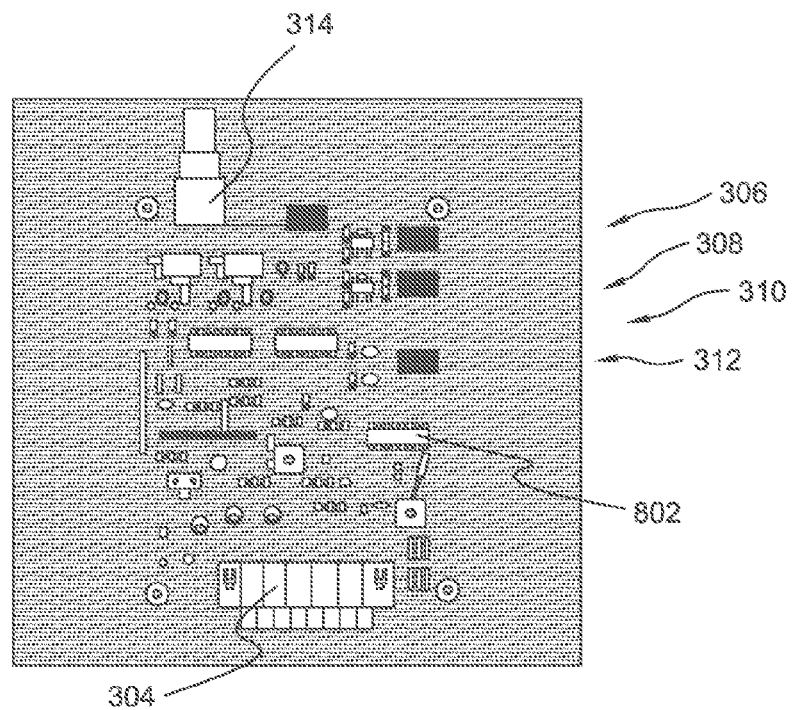
FIG. 16 depicts a control board of the disclosure.
Figure 17:
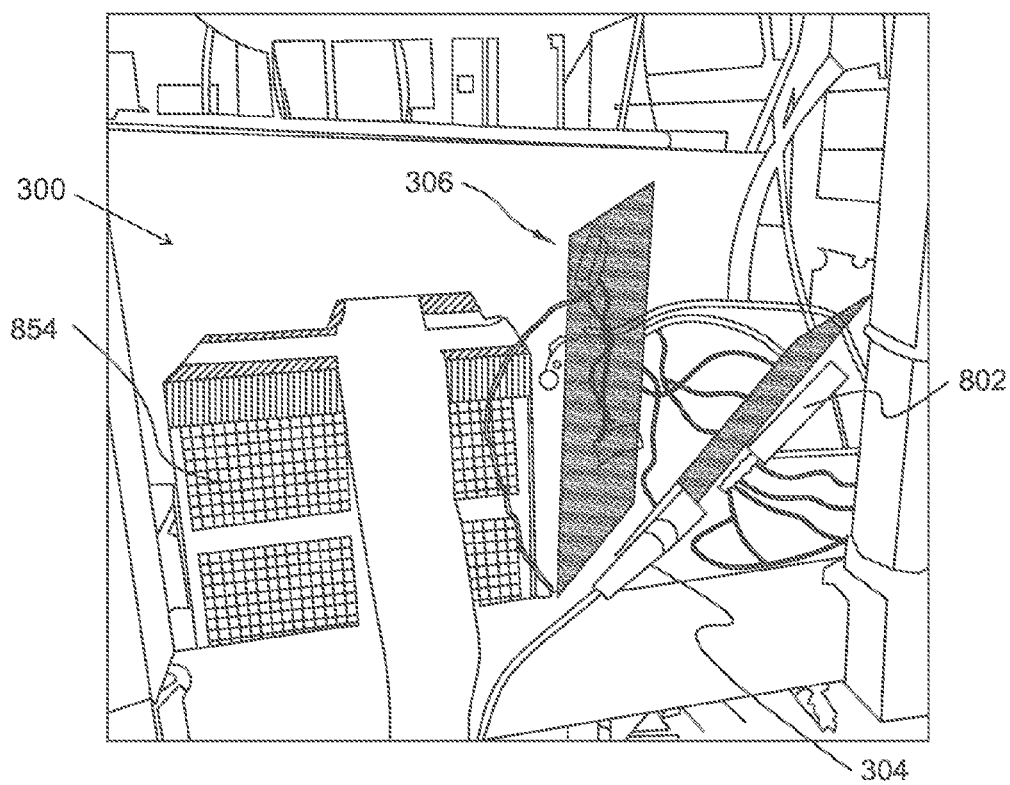
FIG. 17 depicts a signal generator and electronic boards forming a portion of a system of the disclosure.

System 300 may include some or all of the components shown in FIGS. 16-18, which is a block diagram of an electronic device and associated components. In this example, an electronic system 300 is advantageously, but not necessarily, a wireless two-way communication device with data communication capabilities, and optionally voice communication capabilities, useful for example in the event of a breathing emergency. Such electronic devices communicate with a wireless voice or data network 850 using a suitable wireless communications protocol. Wireless voice communications are performed using either an analog or digital wireless communication channel. Data communications allow the system 300 to communicate with other computer systems via the Internet. Examples of electronic devices that are able to incorporate the above described systems and methods include, for example, a data messaging device, a two-way pager, a cellular telephone with data messaging capabilities, a wireless Internet appliance or a data communication device that may or may not include telephony capabilities.

The illustrated system 300 is an example electronic device that includes two-way wireless communications functions. Such electronic devices incorporate communication subsystem elements such as a wireless transmitter 810, a wireless receiver 812, and associated components such as one or more antenna elements 814 and 816. A digital signal processor (DSP) 808 performs processing to extract data from received wireless signals and to generate signals to be transmitted. The particular design of the communication subsystem is dependent upon the communication network and associated wireless communications protocols with which the device is intended to operate. The DSP 808 can additionally or alternatively process audio signals received from a position at or near the neck of a patient, to analyze the signals to determine an appropriate time to trigger a cough or swallow.

The system 300 includes a microprocessor 802 that controls the overall operation of the system 300. The microprocessor 802 interacts with the above described communications subsystem elements and also interacts with other device subsystems such as flash memory 806, random access memory (RAM) 804, auxiliary input/output (I/O) device 838, data port 828, display 834, keyboard 836, speaker 832, microphone 830, a short-range communications subsystem 820, a power subsystem 822, and any other device subsystems.

System 300 further advantageously includes some or all of a frequency generator 308 capable of outputting the therapeutic varying frequency and voltage described herein. Additionally, sensors 306, advantageously including EMG and pressure sensing are provided. The foregoing elements 306 and 308 are advantageously in communication with and or under the control of processor 802, although they may be provided with their own logic and control, or they may be under the control of an external processor or logic circuit. In one embodiment, one or more aspects of elements 306 or 308 may be controlled by a manual adjuster, for example a potentiometer 314 (FIG. 16). Cables 304 or wireless signals connect subunits 306 and 308 to processor 802 or to one or more other logic or control units. Portions of system 300, including subunits 306 and 308 may be provided on one or more separate electronic circuit boards.

A battery 824 is connected to a power subsystem 822 to provide power to the circuits of the system 300. The power subsystem 822 includes power distribution circuitry for providing power to the system 300 and also contains battery charging circuitry to manage recharging the battery 824. The power subsystem 822 includes a battery monitoring circuit that is operable to provide a status of one or more battery status indicators, such as remaining capacity, temperature, voltage, electrical current consumption, and the like, to various components of the system 300.

The data port 828 of one example is a receptacle connector 104 or a connector that to which an electrical and optical data communications circuit connector 800 engages and mates, as described above. The data port 828 is able to support data communications between the system 300 and other devices through various modes of data communications, such as high speed data transfers over an optical communications circuits or over electrical data communications circuits such as a USB connection incorporated into the data port 828 of some examples. Data port 828 is able to support communications with, for example, an external computer or other device.

Data communication through data port 828 enables a user to set preferences through the external device or through a software application and extends the capabilities of the system by enabling information or software exchange through direct connections between the system 300 and external data sources rather than via a wireless data communication network. In addition to data communication, the data port 828 provides power to the power subsystem 822 to charge the battery 824 or to supply power to the electronic circuits, such as microprocessor 802, of the system 300.

Operating system software used by the microprocessor 802 is stored in flash memory 806. Further examples are able to use a battery backed-up RAM or other non-volatile storage data elements to store operating systems, other executable programs, or both. The operating system software, device application software, or parts thereof, are able to be temporarily loaded into volatile data storage such as RAM 804. Data received via wireless communication signals or through wired communications are also able to be stored to RAM 804.

The microprocessor 802, in addition to its operating system functions, is able to execute software applications on the system 300. A predetermined set of applications that control basic device operations, including at least data and voice communication applications, is able to be installed on the system 300 during manufacture. Examples of applications that are able to be loaded onto the system may be a personal information manager (PIM) application having the ability to organize and manage data items relating to the system user, such as, but not limited to, e-mail messages; text messaging; programming therapeutic events; reminding of maintenance tasks; notification of battery charge; setting or revising therapies, including changing frequency patterns, voltage patters, and the timing of therapeutic events; and the transmittal of information to care givers, nurses, or doctors.

Further applications may also be loaded onto the system 300 through, for example, the wireless network 850, an auxiliary I/O device 838, Data port 828, short-range communications subsystem 820, or any combination of these interfaces. Such applications are then able to be installed by a user in the RAM 804 or a non-volatile store for execution by the microprocessor 802.

In a data communication mode, a received signal such as a text message or web page download is processed by the communication subsystem, including wireless receiver 812 and wireless transmitter 810, and communicated data is provided the microprocessor 802, which is able to further process the received data for output to the display 834, or alternatively, to an auxiliary I/O device 838 or the Data port 828. A user of the system 300 may also compose data items, such as e-mail messages, using the keyboard 836, which is able to include a complete alphanumeric keyboard or a telephone-type keypad, in conjunction with the display 834 and possibly an auxiliary I/O device 838. Such composed items are then able to be transmitted over a communication network through the communication subsystem.

For voice communications, overall operation of the system 300 is substantially similar, except that received signals are generally provided to a speaker 832 and signals for transmission are generally produced by a microphone 830. Alternative voice or audio I/O subsystems, such as a voice message recording subsystem, may also be implemented on the system 300. Although voice or audio signal output is generally accomplished primarily through the speaker 832, the display 834 may also be used to provide an indication of the identity of a calling party, the duration of a voice call, or other voice call related information, for example.

Depending on conditions or statuses of the system 300, one or more particular functions associated with a subsystem circuit may be disabled, or an entire subsystem circuit may be disabled. For example, if the battery temperature is low, then voice functions may be disabled, but data communications, such as e-mail, may still be enabled over the communication subsystem.

A short-range communications subsystem 820 provides for data communication between the system 300 and different systems or devices, which need not necessarily be similar devices. For example, the short-range communications subsystem 820 includes an infrared device and associated circuits and components or a Radio Frequency based communication module such as one supporting Bluetooth® communications, to provide for communication with similarly-enabled systems and devices, including the data file transfer communications described above.

A media reader 860 is able to be connected to an auxiliary I/O device 838 to allow, for example, loading computer readable program code of a computer program product into the system 300 for storage into flash memory 806. One example of a media reader 860 is an optical drive such as a CD/DVD drive, which may be used to store data to and read data from a computer readable medium or storage product such as computer readable storage media 862. Examples of suitable computer readable storage media include optical storage media such as a CD or DVD, magnetic media, or any other suitable data storage device. Media reader 860 is alternatively able to be connected to the system through the Data port 828 or computer readable program code is alternatively able to be provided to the system 300 through the wireless network 850.

Figure 19:
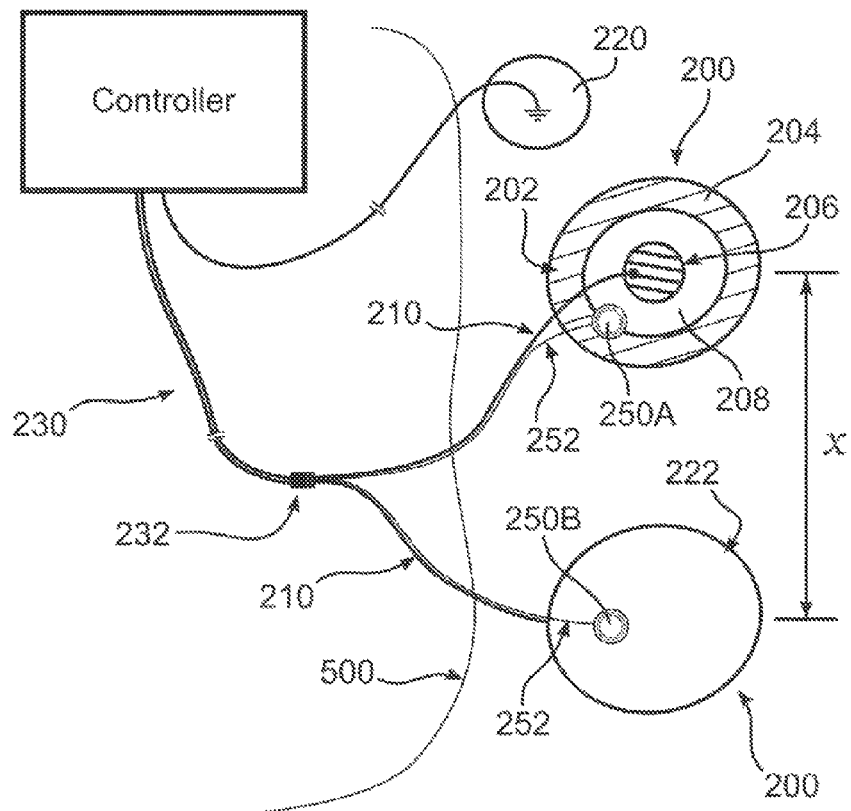
FIG. 19 depicts an assembly including a controller, together with electrodes including integrated microphones, all in accordance with the disclosure.

Referring now to FIG. 19, an electrode 200 includes a patient contacting surface 202, shown in the upper electrode in FIG. 19, having an adhesive surface 204, and a electrical conductor 206. In an embodiment, a conductive material 208, for example a conductive gel, is provided to improve conductivity between the skin and conductor 206. Electrode 200 can have any shape, including for example square, rectangular, circular, or ovoid.

One or more wire conductors 210 extend away from electrode 200, and electrically transmit or receive an electrical signal from the controller. A wireless signal may also transmit signals between electrode 200 and the controller, from a suitable transmitter, not shown, associated with electrode 200. In this configuration, a battery connected to electrode 200 and the wireless transmitter can be provided, operative to generate a stimulating electrical current upon a signal received by the wireless transmitter from the controller.

An audio monitoring device, for example an acoustic signal transducer, or body microphone 250A is positioned to preferentially detect audio signals emanating from a direction of the skin and the interior of the body. It should be understood that the upper electrode in FIG. 19 is illustrated in an inverted state with respect to a functional position upon the skin, so that the patient contacting surface 202 may be understood. In a functional position, shown in the lower electrode 200, microphone 250A faces the skin 500 of the patient. One or more wire conductors 252 extend away from microphone 250A, and electrically transmit audio information to the controller. A wireless signal may also be transmitted from a suitable transmitter, not shown, associated with microphone 250A, not shown.

In an embodiment, one or more of electrode 200 is provided to record EMG readings from the body, which can be analyzed by the controller to determine a therapeutic or appropriate time to trigger a cough or swallow, as described elsewhere herein. The controller may then internally switch electrodes 200 to serve as transmitters for a cough or swallow stimulating signal, as described herein.

One or more ground electrodes 220, which can have a similar or different configuration to electrode 200, can be provided elsewhere upon the body, for example to enable or improve EMG readings, or to provide alternative pathways for a stimulating signal.

Figure 20:
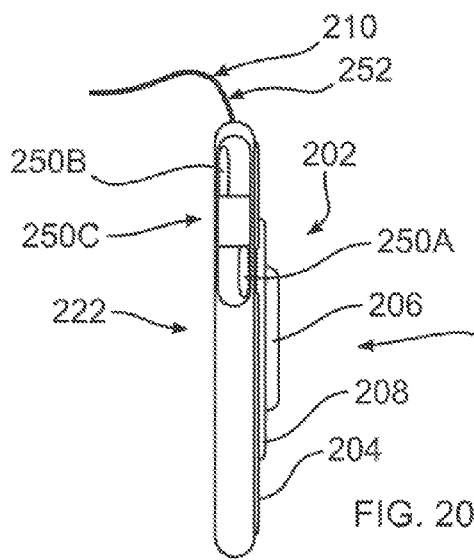
FIG. 20 depicts a cross section of an electrode including a bidirectional microphone, in accordance with the disclosure.
Figure 21:
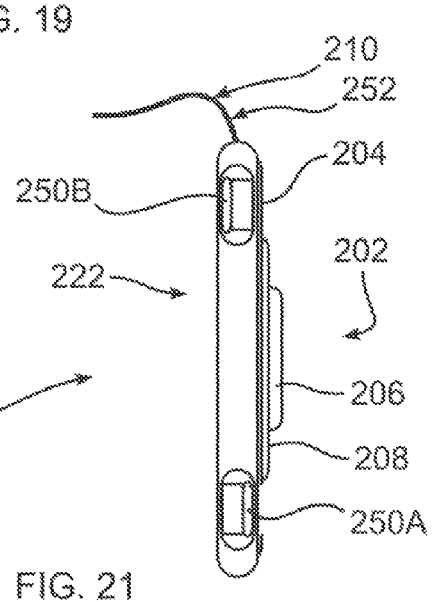
FIG. 21 depicts a cross section of an electrode including two microphones, one facing the body, and one not facing the body, in accordance with the disclosure.

Electrode 200 further includes an environment facing surface 222, shown in the lower electrode in FIG. 19. An environmental microphone 250B can be positioned upon surface 222 to detect audio signals emanating from the environment, outside the body, when electrode 200 is positioned upon skin 500. In an embodiment, microphone 250B forms part of a bidirectional microphone 250C together with microphone 250A, as shown in FIG. 20. In another embodiment, one electrode 200 includes microphone 250A, and another electrode 200 includes microphone 250B. In a further embodiment, a single electrode contains two separate microphones 250A, 250B, as shown in FIG. 21.

FIG. 19 may be construed to depict separate microphones 250A (above) and 250B (below), or a bidirectional microphone in either or both of the upper or lower illustration of electrode 200. Further, while FIG. 19 depicts two electrodes, each containing at least one microphone, only one electrode 200 can be provided with both microphones 250A, 250B.

In all configurations, the controller can receive a first signal including audio information relating to sounds emanating from the body, and a second audio signal including audio information relating to sounds emanating from the environment. The controller may further be configured to synthesize audio information from more than one source of environmental audio information, and or more than one source of audio information from the body.

In an embodiment, two electrodes 200, as illustrated in FIG. 19, are connected by a common cord or cable 230. A tether 232 maintains a maximum separation of electrodes upon skin 500, indicated by arrow "x" in FIG. 19, for example a maximum separation of about 1 inch for adults, although other maximum distances can be established in this manner. Accordingly, electrodes and their associated components may be placed substantially less or substantially greater than one inch apart, however a maximum separation may be established by a configuration of tether 232. A placement of electrodes 200 for stimulating coughing or swallowing is otherwise established as described elsewhere herein. In accordance with the invention, more than one pair of electrodes and associated microphones can be effectively connected to the controller.

Further in accordance with the disclosure, the audio information obtained from body microphone 250A is processed by processor 802 to detect, in an embodiment, pharyngeal sounds, and more specifically, frequency and amplitude information over the behavior production. This audio information can be analyzed, alone or together with other information about the body, to determine that a cough or swallow is beginning, or should take place imminently. For example, sounds correlating with an attempt at coughing or swallowing are characteristic for all individuals, and for a particular patient. Processor 802 can conduct pattern matching for these characteristic sounds, for example using software algorithms, to determine that such behavioral efforts are taking place. If this is indicated, the controller can send a stimulating electrical signal to the electrodes to improve the efficacy of the cough or swallow, by stimulating muscles proximate the electrodes. Alternatively or additionally, a mechanical or fluid stimulus may be applied as described herein, to provide further or alternative stimulation for producing an effective cough or swallow.

The aforedescribed audio information can be analyzed together with EMG information gathered from electrodes 200, or other electrodes, to increase a probability that a cough or swallow is intended or needed. Processor 802 can be configured, for example, to stimulate a cough or swallow only when audio and EMG information both indicate to a first probability that stimulation is needed, or when at least one of audio or EMG information indicates with a second probability, for example a higher probability, that stimulation is needed.

Software executing within processor 802, or upon another processor, can be used in a normalization procedure to enable processor 802 to distinguish frequency and amplitude differences between non-swallow/cough sounds that the patient might produce. For example, audio information can be collected, recorded, and analyzed to form a sound map, which can later be compared with impending, incipient, initial, or ongoing cough or swallow sounds of the patient, which may also be compared with a sound map, to determine that a cough or swallow is occurring or needed. Upon such determination, the controller can stimulate coughing or swallowing using mechanical, liquid, or electrical stimulation as described herein.

Environmental microphone 250B captures audio information of the ambient environment, so that undesired ambient or background noise from the environment may be separated from desired audio information of the body received by body microphone 250A. This improves an ability of processor 802 to compare cough or swallow sounds with template or sound map information, or to distinguish new body audio information from previously recorded or analyzed other body sounds which are not indicative of a cough or swallow. Thus, environmental microphone 250B provides audio information for a background noise reducing or cancelling function of processor 802. This is particularly useful in restaurants and other noisy locations where a patient is apt to eat or drink.

In accordance with an embodiment, a patient, without special skills or training, can attach electrodes 200 to their body, in one embodiment using a template or guide to which electrodes 200 are attached, plug a single cable connected to electrodes 200 and microphones 250A, 250B into the controller, and thereafter rely on the assembly to stimulate an effective cough or swallow as needed, and can effectively function in a noisy environment. Additionally, the detailed physiologic feedback provided by microphones 250A, 250B helps ensure appropriate stimulation for the optimization of cough and swallow. The integrated controller, electrodes 200, and microphones 250A, 250B further enables physician/clinician monitoring of patient progression during therapeutic treatment. In an embodiment, the controller collects any of audio information, EMG information, and information pertaining to stimulation, and transmits this information to experienced medical practitioners for analysis. In this manner, remote analysis is possible, and population areas without such experienced practitioners can benefit from improved care.

A system incorporating any or all of the physical devices described herein is constructed to be sufficiently rugged, simple, and reliable for use in the manner described herein. Thus, the system could include any or all of mechanical stimulation devices, stimulating fluids, electrodes, cables, tethers, microphones, muscle monitor devices such as EMG sensors, electrodes or hereinafter developed muscle monitoring devices, audio monitor devices including microphones, transducers, or hereinafter developed audio monitoring devices, signal or frequency generators, power supplies, computing components and computer control devices, transmitters, receivers, antennae, batteries, power cords, connectors, ports, displays, keyboards, I/O devices, networking devices, media reading devices, media storage devices, and any other device described herein.

All references cited herein are expressly incorporated by reference in their entirety. It will be appreciated by persons skilled in the art that the present invention is not limited to what has been particularly shown and described herein above. In addition, unless mention was made above to the contrary, it should be noted that all of the accompanying drawings are not to scale. There are many different features to the present invention and it is contemplated that these features may be used together or separately. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

REFERENCES

Cabre, M., Serra-Prat, M., Palomera, E., Almirall, J., Pallares, R., & Clave, P. (2010). Prevalence and prognostic implications of dysphagia in elderly patients with pneumonia. *Age and ageing*, 39(1), 39.

Jones, U., Enright, S., & Busse, M. (2011). Management of respiratory problems in people with neurodegenerative conditions: a narrative review. *Physiotherapy*.

Pitts, T., Troche, M. S., Camaby-Mann, G., Rosenbek, J. C., Okun, M. S., & Sapienza, C M. (2010). Utilizing voluntary cough to detect penetration and aspiration during oropharyngeal swallowing in Parkinson's disease. *Chest*.

Smith Hammond, C. A., Goldstein, L. B., Homer, R. D., Ying, J., Gray, L., Gonzalez-Rothi, L., & Bolser, D. C. (2009). Predicting aspiration in patients with ischemic stroke: comparison of clinical signs and aerodynamic measures of voluntary cough. *Chest*, 135(3), 769-777. doi: chest.08-1122 [pii] 10.1378/chest.08-1122

Smith Hammond, C. A., Goldstein, L. B., Zajac, D. J., Gray, L., Davenport, P. W., & Bolser, D. C. (2001). Assessment of aspiration risk in stroke patients with quantiication of voluntary cough. *Neurology*, 56(4), 502-506.

Sue Eisenstadt, E. (2010). Dysphagia and aspiration pneumonia in older adults. *Journal of the American academy of Nurse Practitioners*, 22(1), 17-22.

Van Den Eeden, S. K., et al., Incidence of Parkinson's disease: variation by age, gender, and race/ethnicity. American Journal of Epidemiology, 2003. 157(11): p. 1015-1022.

Brookmeyer, R., S. Gray, and C. Kawas, Projections of Alzheimer's disease in the United States and the public health impact of delaying disease onset. American Journal of Public Health, 1998. 88(9): p. 1337.

Fernandez, H. and K. Lapane, Predictors of mortality among nursing home residents with a diagnosis of Parkinson's disease. Medical science monitor: international medical journal of experimental and clinical research, 2002. 8(4).

Ertekin, C. and J. B. Palmer, Physiology and electromyography of swallowing and its disorders. Suppl Clin Neurophysiol, 2000. 53: p. 148-54.

Jean, A., Brain stem control of swallowing: neuronal network and cellular mechanisms. Physiological Review, 2001. 81(2): p. 929-69.

Canning, B. J., Anatomy and neurophysiology of the cough reflex. Chest, 2006. 129(1 suppl): p. 33S.

Fontana, G. A. and F. Lavorini, Cough motor mechanisms. Respir Physiol Neurobiol, 2006. 152(3): p. 266-81.

Lavietes, M. H., et al., Airway dynamics, oesophageal pressure and cough. Eur Respir J, 1998. 11(1): p. 156-61.

Oku, Y., I. Tanaka, and K. Ezure, Activity of bulbar respiratory neurons during fictive coughing and swallowing in the decerebrate cat. The Journal of Physiology, 1994. 480(Pt 2): p. 309.

Satoh, I., et al., Upper airway motor outputs during sneezing and coughing in decerebrate cats. Neuroscience research, 1998. 32(2): p. 131-135.

Gestreau, C., et al., Activity of dorsal respiratory group inspiratory neurons during laryngeal-induced fictive coughing and swallowing in decerebrate cats. Experimental brain research, 1996. 108(2): p. 247-256.

Lalmohamed A, et al., Causes of death in patients with multiple sclerosis and matched referent subjects: a population-based cohort study. Eur J Neurol., 2012.

Lechtzin N., Respiratory effects of amyotrophic lateral sclerosis: problems and solutions. Respir Care, 2006. 51(8) 871-81.

REFERENCE LIST 104 receptacle connector
200 electrode
202 patient contacting surface
204 adhesive surface
206 electrical conductor
208 conductive material
210 wire conductors (electrodes)
222 environment facing surface
230 cable
232 cable tether
250A body microphone
250B environment microphone
252 wire conductors (microphone)
300 system
304 cables or wireless connection
306 sensors/EMG sensing
308 frequency generator/power supply
500 skin
802 processor(s)
804 RAM
806 flash memory
808 DSP
810 wireless transmitter
812 wireless receiver
814 antenna(s)
816 antenna(s)
820 short-range comm. system
822 power subsystem
824 battery
828 data port
830 microphone
832 speaker
834 display
836 keyboard
838 I/O device
850 data network
860 media reader

What is claimed is:

1. A method of protecting an airway of a patient, comprising:
    monitoring muscle movement information of the patient with a muscle monitoring device;
    monitoring patient audio information using a first acoustic signal transducer positioned upon an electrode and oriented to detect sound emanating from the body of the patient;
    monitoring environmental audio information using a second acoustic signal transducer positioned upon an electrode and oriented to detect sound emanating from an environment outside of the body of the patient;
    electronically processing the patient and environmental audio information to reduce environmental audio information within the patient audio information to improve detection of sounds emanating from the body;
    analyzing the muscle movement information and the electronically processed audio information by at least one electronic device to identify an attempted cough or swallow; and
    applying an electrical stimulus to the neck of the patient using a conductor of an electrode when the analysis indicates an attempted cough or swallow, varying at least one of an amplitude or frequency during the stimulus, the applied electrical stimulus operative to promote an efficacious cough or swallow.

2. The method of claim 1, wherein the electrical stimulus including a voltage within a range of greater than zero volts and less than 20 volts.

3. The method of claim 1, wherein the frequency is varied, and wherein the frequency is swept between at least about 4 Hz to not more than about 30 Hz.

4. The method of claim 1, wherein an electrical stimulus is applied before the patient has attempted to swallow, and an electrical stimulus is applied between about 1 millisecond to about 0.5 seconds after the patient has attempted to swallow or has swallowed.

5. The method of claim 3, wherein the muscle monitoring device is an EMG sensor, and the electrical stimulus is applied after detecting behavior specific markers in an EMG signal of the EMG sensor.

6. The method of claim 1, wherein monitoring muscle movement includes analyzing EMG information of the muscle monitoring device by one or more computer processors, the processors operative to initiate the application of the electrical stimulus.

7. The method of claim 1, wherein the patient may indicate to the at least one electronic device that a swallow or cough is impending.

8. The method of claim 1, wherein the at least one electronic device is at least one computer processor operative to initiate the application of the electrical stimulus.

9. The device of claim 1, wherein the conductor of the electrode is used to gather EMG information.

10. The device of claim 1, wherein the first and second acoustic signal transducer, and the conductor, are positioned upon the same electrode.

11. An airway protection system for protecting an airway of a patient, the system comprising:
    a muscle monitor device configured to communicate information relating to an attempted cough or swallow of the patient;
    a first audio transducer positioned to preferentially receive sounds emanating from the body of the patient with respect to sounds originating in an environment outside the body;
    a second audio transducer positioned to preferentially receive sounds emanating from an environment outside the body with respect to sounds originating within the body;
    at least one computer processor executing software stored on non-transitory media, the software configured for
        analyzing sound information received from the first and second audio transducers to reduce sounds originating in the environment outside the body in the sound information from the first audio transducer,
        analyzing information communicated by the muscle monitor device, and the analyzed sound information, to identify an attempted cough or swallow; and
    a signal generator configured to apply an electrical stimulus to the neck of the patient responsive to the computer processor when the software analysis indicates an attempted cough or swallow, the signal generator configured to vary frequency during the stimulus, the applied electrical stimulus operative to promote an efficacious cough or swallow.

12. The device of claim 11, wherein the signal generator is further configured to maintain a voltage greater than zero.

13. An airway protection system for protecting an airway of a patient, the system comprising:
    a muscle movement sensor configured to communicate information relating to an attempted cough or swallow of the patient;
    an audio monitor device configured to communicate first audio information of sounds emanating from the body of the patient, and second audio information emanating from an environment external to the body of the patient; and
    at least one computer processor executing software stored on non-transitory media, the software configured for analyzing the first and second audio information to reduce sounds emanating from an environment external to the body of the patient that are present in the first audio information, the software further configured to analyze the information communicated by the muscle movement sensor and the analyzed sound information to identify an attempted cough or swallow; and
    a signal generator configured to apply an electrical stimulus to the neck of the patient responsive to the computer processor when the software analysis indicates an attempted cough or swallow, the signal generator configured to vary frequency while maintaining greater than 0 volts during the stimulus, the applied electrical stimulus operative to promote an efficacious cough or swallow.

14. The system of claim 13, wherein the muscle movement sensor comprises at least two electrodes positionable upon skin of the patient, the at least two electrodes configured for capturing electromyographic information and for transmitting a signal from the signal generator to the body.

15. The device of claim 14, wherein the first audio information is obtained from a first microphone attached to at least one of the at least two electrodes, and the second audio information is obtained from a second microphone attached to one of the at least two electrodes.

16. The device of claim 15, wherein the first and second microphones are configured within a single bidirectional microphone.

17. The system of claim 13, wherein the audio monitor device comprises a first microphone positioned to favor the capture of audio information emanating from the body of the patient, and a second microphone positioned to favor the capture of audio information emanating from an environment external to the body.

18. The device of claim 13, wherein the first audio information is obtained from a first audio transducer positioned upon an electrode and oriented to receive sounds emanating from the body of the patient, and the second audio transducer is positioned upon the electrode and is oriented to receive sounds emanating from an environment external to the body of the patient.

19. The device of claim 18, wherein the first audio transducer is positioned upon a first side of the electrode that is adhered to the body, and the second audio transducer is positioned upon a second, opposite side of the electrode relative to the first electrode.

20. The device of claim 13, wherein the signal generator is further configured to vary frequency between 4 and 30 Hz.

* * * * *